(12) United States Patent
Stauch et al.

(10) Patent No.: US 6,565,576 B1
(45) Date of Patent: May 20, 2003

(54) DISTRACTION ASSEMBLY

(75) Inventors: Roman Stauch, Igersheim (DE); Jürgen Klein, Weikersheim (DE)

(73) Assignee: Wittenstein GmbH & Co. KG, Igersheim (DE)

( * ) Notice: Subject to any disclaimer, the term of this patent is extended or adjusted under 35 U.S.C. 154(b) by 0 days.

(21) Appl. No.: 09/857,161

(22) PCT Filed: Nov. 20, 1999

(86) PCT No.: PCT/EP99/08969

§ 371 (c)(1),
(2), (4) Date: Jun. 1, 2001

(87) PCT Pub. No.: WO00/33751

PCT Pub. Date: Jun. 15, 2000

(30) Foreign Application Priority Data

Dec. 4, 1998 (EP) .......................................... 198 56 062

(51) Int. Cl.⁷ ................................................. A61F 2/38
(52) U.S. Cl. .......................................... 606/105; 606/71
(58) Field of Search ............................. 606/71, 57, 53, 606/54, 55, 58, 70, 86, 87, 105, 74

(56) References Cited

U.S. PATENT DOCUMENTS

| 5,626,579 | A | * | 5/1997 | Muschler et al. |
| 5,672,177 | A | * | 9/1997 | Seldin |
| 5,902,304 | A | * | 5/1999 | Walker et al. |
| 6,187,004 | B1 | * | 2/2001 | Fearon |

FOREIGN PATENT DOCUMENTS

WO           WO99/51160           * 10/1999

\* cited by examiner

*Primary Examiner*—Pedro Philogene
(74) *Attorney, Agent, or Firm*—Bachman & LaPointe, P.C.

(57) ABSTRACT

A distraction assembly for the plastic surgery of the face, for correcting the upper and/or lower jaw, for example for removing an overbite, a cross bite, a cleft palate or for bridging bone structure that was removed by, for example, surgery, consists of a device with at least two elements which are axially moveable in relation to each other. The device can be completely implanted subcutaneously and can be indirectly or directly actuated without contact, especially by energy inductively supplied from outside.

6 Claims, 2 Drawing Sheets

DISTRACTION ASSEMBLY

BACKGROUND OF THE INVENTION

The invention relates to a distraction apparatus for plastic surgery of the face, for correcting the upper and/or lower jaw of a skull, for example for rectifying an overbite, crossbite or cleft palate, or for bridging a bone structure which has been lost for example by disease, with an appliance made up of at least two elements which can be moved axially in relation to each other.

Corrections of the jaw, that is to say maxilla and/or mandible, are nowadays mostly undertaken by means of an operation. This operation lasts for about 2 to 3 hours and can only be performed under inpatient conditions. Hospitalization is therefore unavoidable.

Apart from the costly operation which is required, there is often also the disadvantage that frequent corrections can be made only by means of subsequent surgical interventions. This is an additional burden on the patient since interventions of this kind cannot be performed without considerable outlay.

Common diseases of the jaw, in particular of the mandible, caused by tumors, including in the areas of the teeth and the roots of the teeth, particularly also as a result of fistulas, can cause damage to the bone structure of the jaw.

Operations are then necessary which also lead to partial loss of the bone structure. This loss must be compensated, for example by means of appropriate apparatuses and the protracted process of growth. For this purpose it is necessary to carry out corrections after union has taken place, in order to make fine adjustments, for example of the mandible in relation to the maxilla. Surgical aftertreatment of this kind is undesirable since it is a great burden on the patient. After completion of such types of treatment, facial surgery is also a frequent consequence, and one which is undesirable.

Frequent repeat surgery can also result in the development of foci of infection.

It is an object of the present invention to make available a distraction apparatus which eliminates said disadvantages and with which two jaw parts can be moved away from each other in particular in a stepless and time-independent manner. The aim here is to make possible, in a very simple manner, larger correction areas and at the same time ensure a minimal burden on the patient and in particular a minimal systemic burden.

SUMMARY OF THE INVENTION

To achieve this object, the appliance can be fully implanted subcutaneously and can be activated without contact and either directly or indirectly.

In the present invention, a subcutaneous distraction apparatus is in particular operated directly or indirectly, activated contactlessly from outside and fitted in an area of the jaw. The distraction apparatus in this case has an appliance which is preferably made up of two elements, preferably cylinders, which can be moved axially in relation to one another. Receiving seats are provided at the ends and securing elements can engage through these receiving seats. These securing elements pass through the appliance and secure the distraction apparatus to the jaw. The securing elements are connected to the jaw in a detachable manner, so that after distraction treatment has been carried out the appliance can be surgically removed again.

Within the scope of the invention it is also to be possible for individual segments of the bone or jaw to be secured to the distraction apparatus and displaced. For this purpose, receiving seats for securing elements can be provided at any desired locations on the element. A bone segment, for example malpositioned on account of tumor removal, can be held and/or displaced.

However, an important feature of the present invention is that two jaw parts which are separated by a gap can be continuously distracted and moved apart from the outside without contact. This is done by means of induction in which an energy transfer element operates the appliance preferably inductively from the outside. For this purpose, an internal or external actuating device can be assigned to the appliance of the distraction apparatus.

Another feature lying within the scope of the invention is that the energy transfer element is either connected externally to the actuating device or is provided internally in the appliance of the distraction apparatus. In the external configuration, the appliance and its axially movable elements can be made larger since the actuating device and the transfer device operate them from the outside. They communicate with one another via a connection line. However, it is important that the actuating device and the energy transfer element are likewise implanted subcutaneously. In the case of the jaw area, in which there is only very little space for implanting the actuating device and energy transfer device, it has proven particularly expedient to implant these at another site in the body. For example, the chest area or abdominal area is very suitable for this purpose. Only a very thin connection line constitutes the necessary connection for actuating the appliance. The distraction apparatus can then be operated inductively via the energy transfer element. This can be done in individual treatments, and such a correction can always be carried out continuously and without surgical treatment of the patient being necessary.

Moreover, the energy transfer element is also intended to be lodged under the skin either in the near vicinity or in quite different areas of the body in order to operate the appliance. The appliance is preferably operated hydraulically by pressure, in which case corresponding drive means, pistons or the like are moved in the actuating device, for example electromechanically. The elements of the appliance can then be moved apart hydraulically. The appliance can also be operated by means of piezo-driven actuators or by actuators made of shape-memory alloys.

It has also proven particularly expedient to carry out the corrections or distraction continuously at several successive time intervals since the tissue relaxation or slow biological adaptation process require this for more rapid recovery.

Another advantage of complete subcutaneous implantation of the distraction apparatus is that distraction can be monitored and adjusted, for example by X-ray. The corrections can be checked in this way to ensure that the jaw obtains its desired shape.

The present invention offers long-term possibilities of operating distraction apparatuses without additional surgical interventions. This is particularly advantageous when corrections are frequently necessary, in the case of very slow formation of new bone, or on account of growth, for example in children.

BRIEF DESCRIPTION OF THE DRAWINGS

Further advantages, features and details of the invention will become evident from the following description of preferred illustrative embodiments, with reference being made to the drawing, in which.

DETAILED DESCRIPTION

Figure 1:
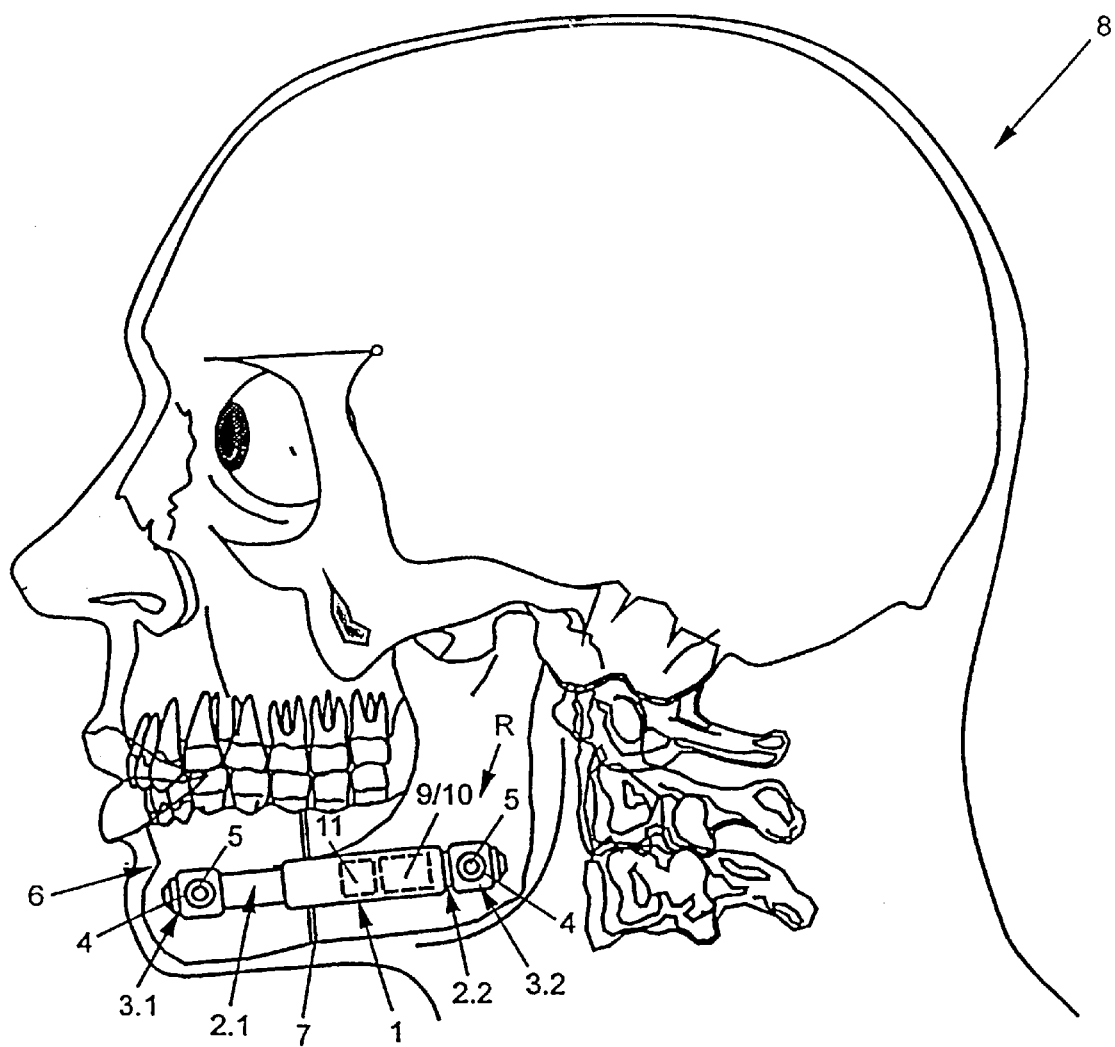
FIG. 1 is a diagrammatic plan view of a distraction apparatus according to the invention in a position of use, fitted in a mandible.

According to FIG. 1, a distraction apparatus R according to the invention has an appliance 1 which consists of preferably two elements 2.1, 2.2 which can be moved axially in relation to one another. In the preferred illustrative embodiment, the elements 2.1, 2.2 are designed as cylinders and can be moved one within the other. However, this is not intended to limit the invention. For example, it is also possible to provide rectangular profiles, rail profiles or the like which can be displaced relative to one another.

At their ends, the elements 2.1, 2.2 have receiving seats 3.1, 3.2 which are provided with an opening 4 (not shown in detail here) through which a securing element 5 engages. The securing element 5 can be fitted in a jaw 6, in particular the mandible, preferably transversely with respect to the appliance 1, and in such a way that it can be removed again. It is also intended that a plurality of receiving seats 3.1, 3.2 can be provided on the element 2.1 and/or element 2.2 at any desired locations and can if appropriate be displaceable for the purpose of securing and/or displacing bone segments.

The appliance 1 is surgically fitted subcutaneously into the jaw 6 of a skull 8. In the present illustrative embodiment, the appliance 1 comprises an actuating device 9 and if appropriate an energy transfer element 10. The actuating device 9 is supplied with energy from and controlled by the energy transfer element 10. It activates a drive means 11 which moves the two elements 2.1, 2.2 of the appliance 1 apart.

In the present illustrative embodiment, the actuating device 9, the energy transfer element 10 and the drive means 11 are only shown diagrammatically. The energy transfer element 10 can consist of a transmitter and the subcutaneously implanted receiver. The transmitter, which is not shown in this illustrative embodiment, can be linked to the receiver in order to start up the appliance 1. In this way the appliance 1, in particular its elements 2.1, 2.2, can be moved apart continuously and in particular contactlessly so that a gap 7 can be widened. This moving-apart can be effected gradually and in particular steplessly without surgical intervention being required for further distraction.

Figure 2:
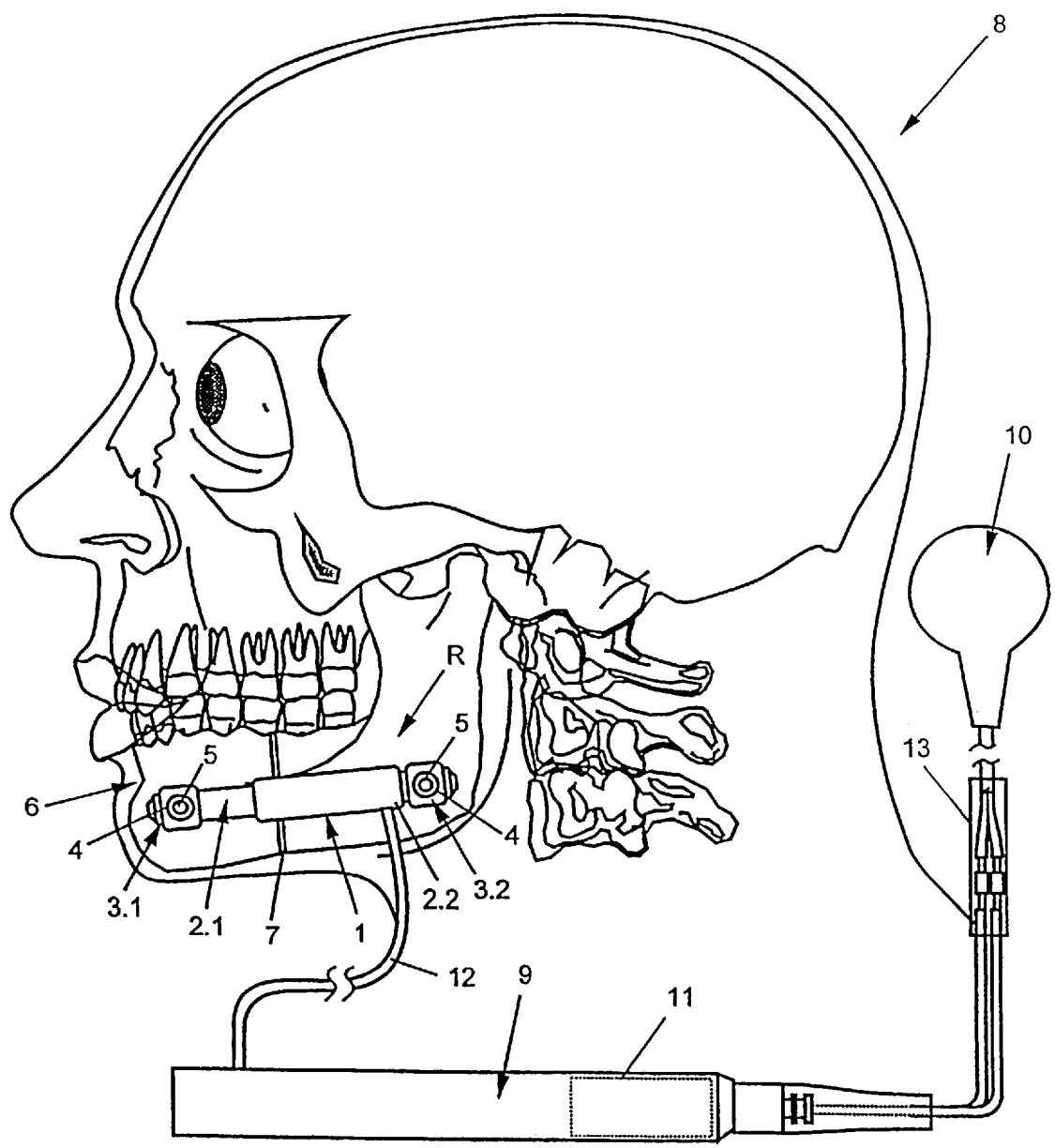
FIG. 2 is a diagrammatic plan view of the distraction apparatus according to FIG. 1, in a position of use and with a separate actuating device.

If very high distraction forces are needed and if the distraction apparatus R is of greater dimensions, the actuating device 9, as is shown in particular in FIG. 2, can also be arranged outside the appliance 1. In this case a connection line 12, which can be of any desired length, establishes a link between the appliance 1 and the actuating device 9. As has been described above, the appliance 1 is made up of two elements 2.1, 2.2 which can be moved preferably axially relative to each other.

However, an important feature of the present invention is that the actuating device 9 and the connection line 12 can likewise be implanted subcutaneously, in which case they can be arranged for example in another area of the body, in the chest area or abdominal area, or even in the back area. The energy transfer element 10 is preferably linked to the actuating device 9 and is likewise implanted subcutaneously in the body. Energy can then be fed from outside contactlessly and inductively via the energy transfer element 10 of the actuating device 9 in order to control and operate the apparatus. The drive means 11 indicated here by broken lines supplies the actuating device 9 with the pressure necessary for moving apart the two elements 2.1, 2.2, in particular cylinders. Distraction takes place in the gap 7.

Another particular feature is a connection point 13 between energy transfer element 10 and actuating device 9. This connection point 13 permits rapid exchange of the energy transfer element 10. The latter can be connected to the actuating device 9 in any desired length, for example, in a very wide variety of distraction apparatuses R. In this way, the distraction apparatus R as a whole can be used in a more universal manner so that the energy transfer element 10 can also be fitted in very favorable areas of the body for purposes of energy transfer and control.

What is claimed is:

1. A distraction apparatus for plastic surgery of the face, for correcting at least one of the upper and lower jaw of a skull, comprising an appliance having at least two elements which are movable axially with respect to each other, each of the at least two elements being secured to a portion of the jaw; an actuating device connected to the appliance for moving the at least two elements, wherein the appliance and the actuating device are fully implanted subcutaneously; and an external energy transfer means for feeding energy inductively to the actuating device for actuating movement of the at least two elements and correspondingly the jaw.

2. The distraction apparatus as claimed in claim 1, wherein the two elements of the appliance can be moved relative to one another by one of mechanical, electromechanical, pneumatical and hydraulical.

3. The distraction apparatus as claimed in claim 1, wherein the two elements are designed as cylinders and can be moved one within the other.

4. The distraction apparatus as claimed in claim 1, wherein the two elements are provided at the ends with receiving seats, into which engage securing elements for detachably securing the appliance to the jaw.

5. The distraction apparatus as claimed claim 1, wherein the two elements can be moved relative to each other via actuators made of shape-memory alloys.

6. The distraction apparatus as claimed in claim 4, wherein a plurality of receiving seats are provided on at least one of the two elements at any desired location, for the purpose of securing and displacing bone segments.

* * * * *